US006894021B2

(12) United States Patent
Belardinelli et al.

(10) Patent No.: US 6,894,021 B2
(45) Date of Patent: May 17, 2005

(54) METHOD FOR IDENTIFYING AND USING A2B ADENOSINE RECEPTOR ANTAGONISTS TO MEDIATE MAMMALIAN CELL PROLIFERATION

(75) Inventors: Luiz Belardinelli, Menlo Park, CA (US); Maria B. Grant, Archer, FL (US)

(73) Assignees: CV Therapeutics, Inc., Palo Alto, CA (US); University of Florida Research Foundation, Gainesville, FL (US)

( * ) Notice: Subject to any disclaimer, the term of this patent is extended or adjusted under 35 U.S.C. 154(b) by 0 days.

(21) Appl. No.: 09/785,895

(22) Filed: Feb. 16, 2001

(65) Prior Publication Data

US 2002/0002142 A1 Jan. 3, 2002

Related U.S. Application Data

(60) Provisional application No. 60/183,141, filed on Feb. 17, 2000.

(51) Int. Cl.[7] .......................... A01N 61/00; A01N 43/90

(52) U.S. Cl. ..................... 514/1; 514/262.1; 514/263.1; 514/263.2

(58) Field of Search ..................... 514/1, 262.1, 263.1, 514/263.2, 2, 44; 435/6, 7.2; 536/23.1, 24.5

(56) References Cited

U.S. PATENT DOCUMENTS

| 4,474,893 | A | 10/1984 | Reading |
| 4,676,980 | A | 6/1987 | Segal et al. |
| 4,816,567 | A | 3/1989 | Cabilly et al. |
| 5,482,856 | A | 1/1996 | Fell, Jr. et al. |
| 5,530,101 | A | 6/1996 | Queen et al. |
| 5,585,089 | A | 12/1996 | Queen et al. |
| 6,060,481 | A | 5/2000 | LaNoue et al. |
| 6,440,933 | B1 * | 8/2002 | Bodor et al. .................. 514/11 |

FOREIGN PATENT DOCUMENTS

| WO | WO 99/42093 | 12/1996 |
| WO | WO 99/38532 | 8/1999 |
| WO | WO 99/42093 | 8/1999 |
| WO | WO 99/38532 | 9/1999 |
| WO | WO 99/63938 | 12/1999 |
| WO | WO 00/51621 | 9/2000 |
| WO | WO 00/73307 | 12/2000 |

OTHER PUBLICATIONS

Yong–Chul Kim et al., Derivaties of the Triazoloquinazoline Adenosine Antagonist (CGS 15943) Having High Potency at the Human A2B and A3 Receptor Subtypes, J. Med. Chem. 1998, 41, pp. 2835–2845.*

Maria B. Grant et al., Adenosine Receptor Activation Induces Vascular Endothelial Growth Factor in Human Retinal Endothelial Cells, Circulation Research, pp. 699–706, Oct. 15, 1999.*

Anders Kvanta et al., Localization of Adenosine Receptor Messenger RNAs in the Rat Eye, Exp. Eye Res. (1997), 65, pp. 595–602.*

B.K. Kemp et al., Adenosine mediates relaxation of human small resistance–like coronary arteries via A2B receptors, British Journal of Pharmacology (1999) 126, pp. 1796–1800.*

W. Michael Flanagan et al., Cellular penetration and antisense activity by a phenoxazine—substituted heptanculeotide. RESEARCH, pp. 1–5.*

Andrea D. Branch, A good antisense molecule is hard to find, TIBS 23—Feb. 1998, pp. 45–50.*

(Continued)

*Primary Examiner*—Karen A. Lacourciere
(74) *Attorney, Agent, or Firm*—McDonnell Boehnen Hulbert & Berghoff LLP

(57) ABSTRACT

This invention concerns methods for identifying $A_{2B}$ adenosine receptor agonists and antagonists as well as methods for using $A_{2B}$ adenosine receptor antagonists to treat cell proliferation orders mediated by the $A_{2B}$ adenosine receptor.

6 Claims, 3 Drawing Sheets

OTHER PUBLICATIONS

K. N. Klotz et al., Comparative pharmacology of human adenosine receptor subtypes—characterization of stably transfected receptors in CHO cells, Naunyn—Schmiedeberg's Arch Pharmacol (1998) 357 pp. 1–9.*

J Lahdenranta et al., Proc. Natl. Acad Sci USA, "An anti–aniogenic state in mice and humans with retinal photoreceptor cell degeneration," 2001, vol. 98, pp. 10368–10373.*

DDF Ma et al, Biotechnology Annual Review, "Synthetic oligonucleotides as therapeutics: the coming of age,"2000, vol. 5, pp. 155–196.*

S Agrawal et al., Molecular Medicine Today, "Antisense therapeutics: is it as simple as complementary base recognition?" Feb. 2000, vol. 6, pp. 72–81.*

DW Green et al., American College of Surgeons, "Antisense Oligonucleotides: An Evolving Technology for the Modulation of Gene Expression in Human Disease," Jul. 2000, vol. 191, No. 1, pp. 93–105.*

K–Y Jen et al., Stem Cells, "Suppression of Gene Expression by Targeted Disruption of Messenger RNA: Available Options and Current Strategies," 2000, 18:307–319.*

Y Cao, International Journal of Biochemistry & Cell Biology, "Endogenous angiogenesis inhibitors and their therapeutic implications," 2001, 33, pp. 357–369.*

Feoktistov et al. Adenosine A2b Receptors evoke Inerleukin–8 Secretion in Human Mast Cells. J. Clin. Invest. vol. 96, Oct. 1995, pp. 1979–1986.*

Yan et al. TGF–B1 Induces Retinal Endothelial Apoptosis. Journal of Cellular Biochemistry. vol. 70, Issue 1, 1998, pp. 70–83.*

Mino, et al., "Adenosine $A_{2B}$ Receptor Inhibition Decreases Retinal Neovascularization in Mice with Oxygen Induced Retinopathy", IOVS, 2000.

Grant, et al., "Proliferation, Migration and ERK Activation in Human Retinal Endothelial Cells through $A_{2B}$ Adenosine Receptor Stimulation", Investigative Opthalmology & Visual Science, vol. 42, No. 9, pp. 2068–2073, 2001.

Grant, et al., "Adenosine Receptor Activation Induces Vascular Endothelial Growth Factor in Human Retinal Endothelial Cells", Circulation Research, pp. 699–706 (1999).

Bailey, (1994) Methods Mol. Biol. 32:381–88.

Dean, (1994) Methods Mol. Biol. 32:361–79.

Dean, (1998) Methods Mol. Biol. 80:23–37.

Dreckhahn et al. (1993) Methods Cell 37:7–56.

Gullick, (1994) Methods Mol. Biol. 32:289–99.

Jones et al., (1986) Nature 321:522.

Kohler & Milstein, (1975), Nature, 256:495.

Morrison, (1992) Ann. Rev. Immunol. 10:239–65.

Presta, (1992) Curr. Op. Struct. Biol. 2:593.

Reichmann et al., (1988) Nature 332:323.

Reisner et al., (1998) Trends in Biotechnol. 16:242–246.

Spira et al., (1984) J. Immunolog. Meth. 74:307.

Steplweski et al., (1985) P.N.A.S. U.S.A. 82:8853.

Wright et al., (1992) Crit. Rev. Immunol. 12:125–68.

International Search Report for International Application PCT/US02/25713.

B.K. Kemp et al., Adenosine mediates relaxation of human small resistance–like coronary arteries via A2B receptors, British Journal of Pharmacology (1999) 126, pp. 1796–1800.*

* cited by examiner

METHOD FOR IDENTIFYING AND USING A2B ADENOSINE RECEPTOR ANTAGONISTS TO MEDIATE MAMMALIAN CELL PROLIFERATION

This application claim priority to U.S. Provisional Patent Application No. 60/183,141, filed on Feb. 17, 2000, the specification of which is incorporated herein by reference.

BACKGROUND OF THE INVENTION

(1) Field of the Invention

This invention concerns methods for identifying $A_{2B}$ adenosine receptor agonists and antagonists as well as methods for using $A_{2B}$ receptor antagonists to treat cell proliferation disorders mediated by the $A_{2B}$ adenosine receptor.

(2) Description of the Art

Adenosine is released by hypoxic tissues and is believed to be an angiogenic factor that links altered cellular metabolism caused by $O_2$ deprivation to compensatory angiogenesis. Adenosine binds to four subtypes of G protein-coupled receptors termed $A_1$, $A_{2A}$, $A_{2B}$ and $A_3$. The nucleoside adenosine has been implicated in angiogenesis. Specifically, it has been demonstrated that adenosine activation of the $A_{2B}$ adenosine receptor (AdoR) increased cAMP accumulation, cell proliferation and VEGF expression in human retinal endothelial cells (HREC). It has been previously reported that the activation of $A_{2B}$ AdoR increased vascular endothelial cell growth factor (VEGF) mRNA and protein expression in human retinal endothelial cells (HREC). Adenosine also has a synergistic effect with VEGF on retinal endothelial cell proliferation and capillary morphogenesis in vitro.

Microvascular abnormalities of the retina, such as retinopathy or prematurity, macular degeneration and diabetic retinopathy are among the leading causes of non-traumatic blindness. These diseases are characterized by neovascularization that results from ischemic injury to retinal vessels, i.e., compensatory angiogenesis. Thus one possible therapy for treating these diseases is to inhibit neovascularization.

SUMMARY OF THE INVENTION

In one embodiment, this invention is a method for inhibiting the proliferation of mammalian cells that express the $A_{2B}$ adenosine receptor comprising administering a therapeutically effective amount of an $A_{2B}$ adenosine receptor antagonist to the mammal.

In another embodiment, this invention is a method for assaying compounds to determine if they are $A_{2B}$ adenosine receptor antagonists or $A_{2B}$ adenosine receptor agonists. The method includes preparing a first and second sample of human retinal endothelial cells; adding a compound to be tested to the first sample of human retinal endothelial cells and allowing the compound to remain in contact with the first sample of human retinal endothelial cells for a defined period of time; and comparing the number of new cells grown in the first sample with the number of new cells grown in the second sample.

In yet another embodiment, this invention includes $A_{2B}$ adenosine receptor agonist or antagonist compounds identified by the methods of this invention.

SUMMARY OF ABBREVIATIONS

Figure 1A:
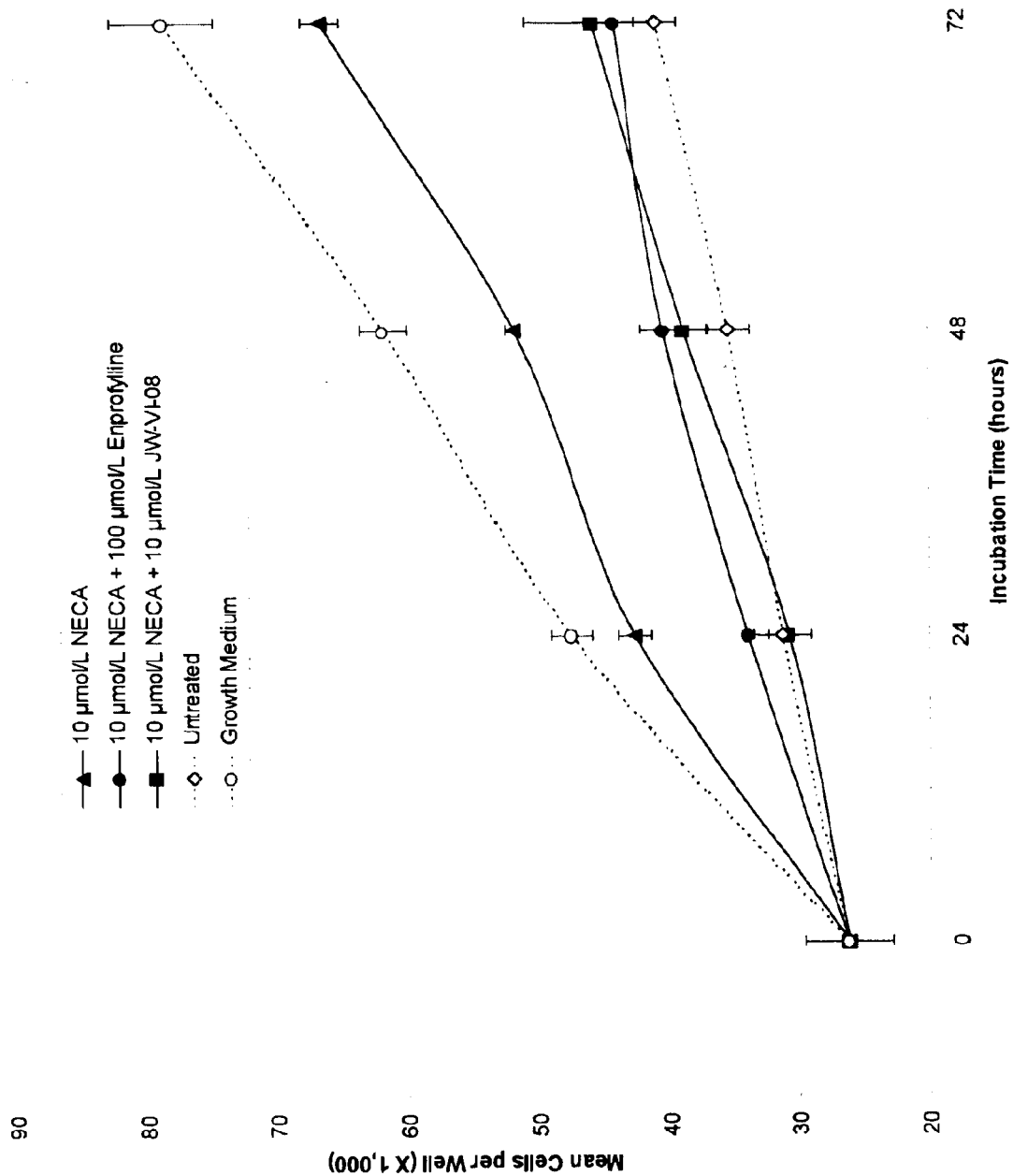
FIG. 1A is a plot of the time course of NECA (10 μmol/L) induced HREC proliferation. The proliferation effect of NECA is completely blocked by either $A_{2B}$-specific antagonists 3-N-propylxanthine (10 μmol/L) or JW-V1-08 (10 μmol/L)

HREC—Human retinal endothelial cells
AdoR—Adenosine receptor
NECA—5'-N-ethylcarboxamido-adenosine
ADA—Adenosine deaminase
JW-V 1-08—3-isobutyl-8-pyrrolidinoxanthine
LDL—Low density lipoprotein
SFM—Serum Free Medium
VEGF—Vascular endothelial growth factor

DESCRIPTION OF THE CURRENT EMBODIMENT

The present invention relates to methods for identifying useful $A_{2B}$ adenosine receptor antagonists. This invention also includes $A_{2B}$ adenosine receptor antagonists identified by the methods of this invention as well as methods for inhibiting cell proliferation in mammals using $A_{2B}$ adenosine receptor antagonists.

One aspect of this invention is methods for screening and identifying compounds that are $A_{2B}$ adenosine receptor agonists and antagonists. The compounds identified by the methods of this invention may include organic compounds, inorganic compounds, oligonucleotides, antisense oligonucleotides, ribozymes, proteins, enzymes, antibodies, and any other compounds or compositions that are amenable to evaluation by the screening methods of this invention.

One method for evaluating compounds as potential $A_{2B}$ adenosine receptor antagonists or agonists of this invention is an in vitro assay that measures the ability of a compound to promote or inhibit the growth of human retinal endothelial cells (HREC). The assay is described in detail in Example 1. Compounds are screened using the assay by comparing the growth of human retinal endothelial cells exposed to the compound in question to the growth of human retinal endothelial cells in a standard solution or in the presence of a standard compound. Compounds that stimulate the growth of human retinal endothelial cells in comparison to the standard are $A_{2B}$ adenosine receptor agonists while compounds that inhibit human endothelial cells growth in comparison to the standard are $A_{2B}$ adenosine receptor antagonists.

A second assay that is useful for identifying $A_{2B}$ adenosine receptor antagonists and agonists is an in vivo mouse assay. In the mouse model, one week old C57BL/6J mice are exposed to 75% oxygen for five days and then to room air. Five days after returning to normal oxygen conditions the mice develop quantifiable retina neovascular tufts. Compounds are evaluated in the screening method by administering the compound in question interperitonealy (IP) to a mouse and then comparing the quantity of neovascular tufts in the eyes of the treated mouse with the quantity of neovascular tufts in the eyes of an untreated mouse. Compounds that inhibit the growth of neovascular tufts in vivo are $A_{2B}$ adenosine receptor antagonists.

Another important aspect of this invention is the discovery that $A_{2B}$ adenosine receptor antagonists are useful in treating mammalian cell proliferation disorders. Such disorders include, but are not limited to vascular endothelial cell proliferation, cancer, restenosis, host graft rejection, gout, general inflammation, and other proliferative disorders.

We have found that $A_{2B}$ adenosine receptor antagonists are particularly useful for inhibiting the growth of vascular endothelial cells which include but not limited to coronary endothelial cells, endothelial cells from the vascular bed, tumor endothelial cells, retinal endothelial cells, dermal endothelial cells, and so forth. A preferred method of this invention includes treating diseases associated the proliferation of retinal endothelial cells (aberrant neovascularization) such as diabetic retinopathy and retinopathy of prematurity. The $A_{2B}$ adenosine receptor antagonists used may be a non-selective $A_{2B}$ adenosine receptor antagonists, they may be a selective $A_{2B}$ adenosine receptor antagonists or they may include a combination of $A_{2B}$ adenosine receptor antagonists.

Methods of this invention for inhibiting cell proliferation and in particular inhibiting endothelial cell proliferation using $A_{2B}$ adenosine receptor antagonists are applicable to any mammal. However, it is preferred that the methods of this invention are used to treat humans. The methods of this invention are performed using pharmaceutically effective amounts of one or more compounds that are $A_{2B}$ adenosine receptor antagonists. Depending on their intended use, the compositions may be in the form of solid, semi-solid or liquid dosage forms, such as, for example, tablets, suppositories, pills, capsules, powders, liquids, suspensions, gases, drops, salves, or the like. One class of preferred dosage forms are solid, semi-solid, or liquid dosage forms that are administered orally in precise dosages. The compositions may include one or more conventional pharmaceutical excipients and at least one active compound of this invention or the pharmaceutically acceptable salts thereof and, in addition, may include other medicinal agents, pharmaceutical agents, carriers, adjuvants, diluents, etc.

For solid compositions, conventional non-toxic solid include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administrable compositions can, for example, be prepared by dissolving, dispersing, etc. an active compound as defined above and optional pharmaceutical adjuvants in a excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound(s), a therapeutically effective amount, i.e. in an amount effective to alleviate the symptoms of the subject being treated. For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%–95% active ingredient, preferably 1–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

When used to treat retinal endothelial cells, the compositions of this invention may be incorporated into eye drops by, for example, combining one or more $A_{2B}$ adenosine receptor antagonists with a physiologically compatible saline solution or gel which is then applied directly to the eyes on a regular basis.

The amount of active compound administered will, of course, be dependent on the subject being treated, the subject's weight, the severity of the affliction, the manner of administration and the judgment of the prescribing physician. However, an effective dosage is in the range of about 1 microgram to about 50 milligram/kg/day. More preferably, an effective, dosage will range from about 1 microgram/kg/day. Since many of the effects of the compounds herein are achieved through a similar mechanism dosages are all generally within the same general and preferred ranges for all these utilities.

Generally, $A_{2B}$ adenosine receptor antagonists will be administered in the methods of this invention in a therapeutically effective amount, i.e., a dosage sufficient to effect treatment. The amount of active compound administered will, of course, be dependent on the subject treated, the subject's weight, the severity of the affliction, the route of administration and the judgement of the prescribing physician. In addition, the dosing frequency will depend up of the method of administration, the affliction being treated, and the degree of affliction being treated. For example, eye drops including an $A_{2B}$ adenosine receptor antagonists can be administered on a regular schedule of from once to 6 times a day or even more frequently when treating retinal endothelial cells.

The administration of $A_{2B}$ adenosine receptor antagonists to mammals to treat cell proliferation disorders is not limited to those methods disclosed above that broadly includes any methods known in the art for administering pharmaceutically active compounds and therapeutic agents to mammals.

It is within the scope of this invention to administer one or more compounds of this invention to a mammal, and preferably to a human by other known routes of pharmaceutical dosage form administration including, but not limited to by bolus, intravenously, transdermally, through inhalation, sub-cutaneously, orally, parenteraly, nasally, in eye drops, by using micropumps or by any other therapeutic agent administration method or route know to one skilled in the art.

EXAMPLE 1

In the present example, we evaluated the role of the $A_{2B}$ is receptor by examining the effects of selective $A_{2B}$ AdoR antagonists on AdoR-mediated HREC proliferation, capillary tube formation and signal transduction pathways.

Method Summary: HREC were exposed to the adenosine analogue 5'-N-ethylcarboxamido-adenosine (NECA) in the absence or presence of AdoR antagonists. Migration was measured using Boyden chambers. Proliferation was assessed by counting. The effect of AdoR activation on tube formation was studied using cells grown on Matrigel.

Materials and Method

Cell Culture

Primary cultures of HREC were prepared and maintained as previously described and cells in passage 3–6 were used for these studies. The identity of endothelial cells in cultures was validated by demonstrating endothelial cell incorporation of fluorescent-labeled acetylated LDL and by flow cytometry analysis as previously described. To maintain purity of HREC, several precautionary steps were taken. HREC were grown in plasma-derived serum, which is free of platelet derived growth factor and does not promote the growth of pericytes (the contaminating cell type in these preparations). In addition, cultures of HREC were exposed to trypsin for only 45 sec prior to passage. Endothelial cells float off during this short trypsin treatment while pericytes remain attached to the substrate.

Proliferation Assay

HREC were seeded at 10 cells/cm in 24 well plates and allowed to adhere overnight. Cells were washed in Hank's balanced salt solution and the medium was replaced with serum—and growth supplement-free medium (SFM) for 24 hr to induce cell-cycle arrest. Cells were washed again and pre-treated with 1 U/mL adenosine deaminase (ADA) for 30 min. Cells were the exposed to NECA (10 $\mu$mol/L) with or without 3-N-propylxanthine (10 $\mu$mol/L) or JW-V1-08 (10 $\mu$mol/L), which exhibit greater selectivity for the $A_{2B}$ receptor than other available antagonists. Controls were HREC exposed to SFM or normal growth medium. For the next three days at 24-hour intervals replicate wells were treated with trypsin and the cells were collected and counted using a Coulter Counter. Each condition was examined in triplicate in three separate experiments using cells from different donors for each experiment.

Chemotaxis

Endothelial cell chemotaxis was measured in blind-well chemotaxis chambers (Neuroprobe, Inc, Bethesda, Md.) as previously described. Briefly a single cell suspension of endothelial cells (3.0×10 cells/well) was prepared and treated with ADA (1 U/mL). Thirty microliters of this suspension was placed in each of 48 lower wells of the blind-well apparatus. The wells were overlaid with a porous (5 $\mu$m diameter pore) polyvinyl—and pyrrolidone-free polycarbonate membrane (Nucleopore, Pleasanton, Calif.), coated with 0.1% dermal collagen. The cells were allowed to attach to the membrane by inverting the chamber of 2 h. The chambers were then placed upright and exposed to NECA alone (10 $\mu$mol/L), NECA combined with 3-N-propylxanthine (10 $\mu$mol/L), JW-V1-08 (10 $\mu$mol/L) or the non-selective AdoR antagonist xanthine amine congener (XAC, 10 $\mu$mol/L) in a 50 $\mu$L volume. After incubation for 12 h, the membrane was recovered and scraped free of cells on the attachment side. The remaining cells, those that had migrated through the pores, were fixed in methanol, is stained with modified Wright's stain and then counterstained with haematoxylin and eosin. The positive control was 10% fetal bovine serum and the negative control was 1% ablumin. Chemokinesis, the non-oriented increase in cell migration in response to a stimulus, was measured by adding equal concentration of NECA or NECA plus one of the antagonists to both lower and upper chambers. Treatment conditions were examined in triplicate in three separate experiments.

Matrigel Assay

Endothelial tube formation was assessed on Matrigel. Briefly, Matrigel was thawed and kept at 4° C. Multi-well plates and pipette tips were chilled to −20° C. and Matrigel (125 $\mu$L) was added to each well of a 48-well plate and allowed to harden for a minimum of 1 h at 37° C. HREC were dissociated enzymatically (2 min at 37° C. in 0.25% Trypsin-EDTA), centrifuged (300×g, 5 min) and re-suspended in serum-free media. Test agents (100 $\mu$L) were prepared at 2× final concentration and 100 $\mu$L were added to wells. HREC (3×10 in 100 $\mu$L per well) were then added and plates were incubated at 37° C. Wells were photographed 48 h after plating. Identical fields in each well were photographed to minimize the possible variation due to variable cell density caused by the settling of cells. Photographs were digitized and image analysis software (Scion Image) was used to measure total tube length in a predefined, comparable area from each well. All conditions were tested in duplicate wells in three separate experiments using cells from different donors.

Results

Cell Proliferation in Response to NECA and AdoR Antagonists

NECA (10 $\mu$mol/L) induced a time-dependent increase in HREC proliferation as measured by cell counts, achieving about 80% of the density of cells exposed to normal growth medium for 3 days. Both of the selective $A_{2B}$ AdoR antagonists tested, 3-N-propylxanthine at 10 $\mu$mol/L and JW-V1-08 at 10 $\mu$mol/L, completely block the proliferative effect of NECA (FIG. 1A).

Effect of NECA and AdoR Antagonists on HREC Migration

Figure 1B:
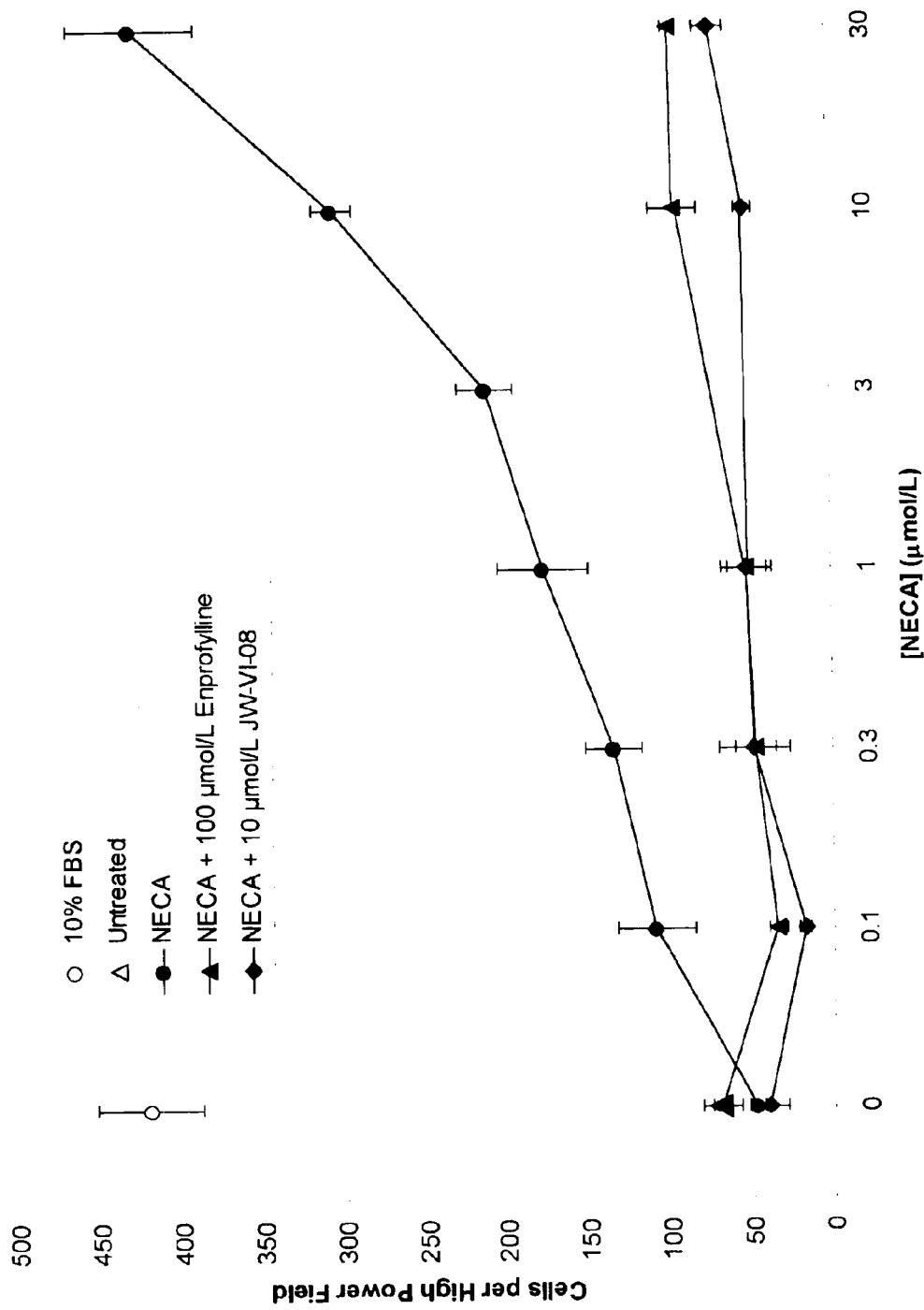
FIG. 1B is a plot of NECA induced concentration-dependent increase in HREC migration compared to unstimulated cells (MEM, minimal essential medium). Values for NECA-induced proliferation and migration are significantly different (p<0.05, by ANOVA) from unstimulated cells.

NECA stimulated HREC chemotaxis when measured in the Boyden chamber assay. NECA increased migration in a concentration-dependent manner. The simultaneous addition of NECA and the selective AdoR antagonist XAC abolished NECA-stimulated migration of HREC. Likewise, co-addition of NECA with either the selective $A_{2B}$ antagonists JW-V1-08 or 3-N-propylxanthine also antagonized the stimulatory effect of NECA on chemotaxis (FIG. 1B). Neither NECA alone nor NECA in combination with the AdoR antagonists induced chemokinesis.

Effect of NECA on Endothelial Cell Tube Formation

Figure 2A:
FIGS. 2A, 2B, 2C and 2D are photomicrographs of endothelial cell tube formation on Matrigel. All micrographs were taken at 48 hr. Unstimulated control cells (4A) show some tube formation by 48 hr. At 48 hr NECA supports extensive tube formation (4B). By contrast, the $A_{2B}$ selective antagonists JW-V1-08 at 10 μmol/L (4 C) and 3-N-propylxanthine at 10 μmol/L (4 D) both diminished NECA-induced tube formation. All micrographs are typical of results seen for cells from three separate donors.
Figure 2B:
Figure 2C:
Figure 2D:
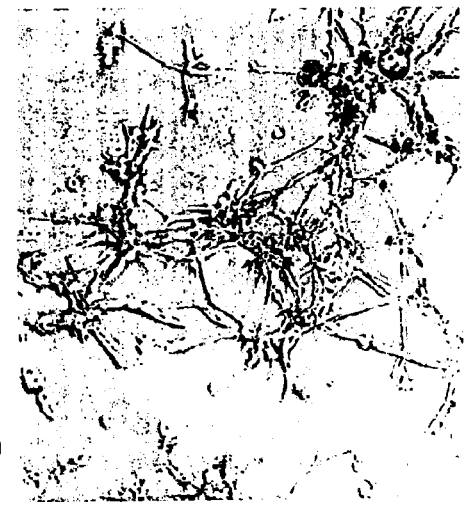

FIG. 4 shows representative photomicrographs of endothelial cell tube formation on Matrigel in the absence or presence of NECA alone or in combination with AdoR antagonists. Some tube formation was evident after 48 h with unstimulated control cells (FIG. 2A). NECA (10 $\mu$mol/L) treatment supported extensive tube formation (FIG. 2B) that was inhibited 2by JW-V1-08 (FIG. 2C). At 48 hr 3-N-propylxanthine (FIG. 2D) inhibited tube formation, resulting in fewer tubes of shorter length.

Total tube length was measured on digitized photographs as pixel length. NECA increased tube length more than 2-fold greater than untreated cells (74.2±2.4 versus 35.7±1.6, respectively, p<0.01). The addition of either 3-N-propylxanthine or JW-V1-08 decreased, but did not completely negate, the NECA-induced tube length (53.7±0.9 and 66±1.2, respectively, both p<0.01).

Summary: NECA induced proliferation in a concentration-dependent manner that was inhibited by the selective $A_{2B}$ AdoR antagonists 3-N-propylxanthine and JW-V1-08. NECA stimulated chemotaxis in a concentration-dependent manner. Both antagonists blocked the effect of NECA on migration. NECA enhanced tube formation on Matrigel while both $A_{2B}$-selective antagonists attenuated this effect.

The results above show that selective $A_2$ AdoR antagonists inhibited NECA-stimulated proliferation, migration and capillary tube formation. $A_{2B}$ AdoR inhibition offers a way to inhibit angiogenesis, and in particular retinal angiogenesis, and provides a novel therapeutic approach to treat diseases associated with aberrant neovascularization such as diabetic retinopathy and retinopathy of prematurity.

The results of Example 1 also show that the adenosine analogue NECA stimulates key steps relevant to angiogenesis. NECA stimulated cell migration (as assessed by Boyden chamber assay) and capillary tube formation (as assessed by the Matrigel assay). NECA also stimulated signaling cascades associated with cell survival and proliferation. The selective $A_2$ antagonists we used attenuated or abolished these effects. These findings suggest that selective adenosine $A_{2B}$ AdoR antagonists can attenuate endothelial cell proliferation leading to the aberrant angiogenesis seen in diabetic retinopathy. Consequently, $A_{2B}$ AdoR antagonists represent a novel therapeutic approach to modulate aberrant retinal neovascular responses.

We claim:

1. A method for inhibiting the proliferation of mammalian retinal endothelial cells comprising administering a therapeutically effective amount of 3-N-propylxanthine to the mammalian retinal endothelial cells, whereby the proliferation of the mammalian retinal endothelial cells is inhibited.

2. The method of claim 1 wherein the 3-N-propylxanthine is administered in an amount ranging from about 1 microgram/kg to about 50 miligrams/kg.

3. The method of claim 1 wherein the 3-N-propylxanthine is administered in an amount ranging from about 1 microgram/kg to about 10 miligrams/kg.

4. The method of claim 1 wherein the 3-N-propylxanthine is administered by a method selected from the group consisting of orally, nasally, transdermally, by bolus, intravenously, in eye drops, by inhalation, and by using micropumps.

5. The method of claim 1 wherein the 3-N-propylxanthine is administered in eye drops.

6. The method of claim 1 wherein the mammal is a human.

* * * * *